United States Patent [19]

Fahmy

[11] Patent Number: 4,804,654
[45] Date of Patent: Feb. 14, 1989

[54] CERTAIN N-(R-SULFONYL) PHOSPHONAMIDOTHIOATES AND DITHIOATES

[75] Inventor: Mohamed A. H. Fahmy, Wilmington, Del.

[73] Assignee: E. I. Du Pont de Nemours and Company, Wilmington, Del.

[21] Appl. No.: 17,165

[22] Filed: Mar. 4, 1987

Related U.S. Application Data

[63] Continuation-in-part of Ser. No. 848,596, Apr. 7, 1986, abandoned.

[51] Int. Cl.$^4$ .............. C07F 9/44; C07F 9/65; A01N 57/20; A01N 57/30
[52] U.S. Cl. .................. 514/90; 514/89; 514/95; 514/117; 514/126; 514/127; 514/128; 544/157; 546/22; 549/6; 558/171; 558/175; 558/185; 558/193; 558/195
[58] Field of Search .......... 564/12; 558/171, 175, 558/185, 193, 195; 514/117, 126, 127, 128, 89, 90, 95; 544/150; 546/245, 246, 264, 22; 549/68, 6

[56] References Cited

U.S. PATENT DOCUMENTS

| | | | |
|---|---|---|---|
| 4,122,174 | 10/1978 | Saito et al. | 558/175 X |
| 4,134,979 | 1/1979 | Kishino et al. | 424/215 |
| 4,150,155 | 4/1979 | Kishino et al. | 514/127 X |
| 4,161,524 | 7/1979 | Kishino et al. | 514/127 X |
| 4,190,652 | 2/1980 | Hofer et al. | 424/222 |
| 4,390,529 | 6/1983 | Fahmy | 424/220 |

OTHER PUBLICATIONS

A. A. Neimysheva et al., Journal of General Chemistry, U.S.S.R. (English), 1966, vol. 36, pp. 520–525.
G. Weisz and G. Schulze, Annalen Der Chemie, vol. 729, pp. 40 to 51, (1969).

Primary Examiner—Richard L. Raymond
Assistant Examiner—Carolyn Greason
Attorney, Agent, or Firm—James A. Costello

[57] ABSTRACT

Compounds of the formula

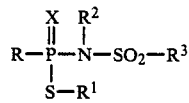

wherein the symbols have assigned meanings, and their use as insecticides and/or miticides.

3 Claims, No Drawings

CERTAIN N-(R-SULFONYL) PHOSPHONAMIDOTHIOATES AND DITHIOATES

CROSS-REFERENCE TO RELATED APPLICATION

This is a continuation-in-part of copending application bearing U.S. Ser. No. 848,596 filed on Apr. 7, 1986.

DESCRIPTION OF THE INVENTION

It has been found that insecticidal and acaricidal activity is possessed by compounds of the formula

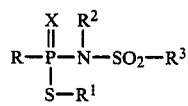 (I)

wherein X is oxygen or sulfur;

R is alkyl or alkenyl of up to twenty carbon atoms, phenyl, or phenalkyl of up to ten carbon atoms;

$R^1$ is alkyl, or alkenyl of up to six carbon atoms, or phenalkyl of up to ten carbon atoms;

$R^2$ is alkyl, alkenyl, alkynyl, haloalkyl or alkylthioalkyl of up to ten carbon atoms; napthyl, pyridyl, or thienyl; phenyl, or phenalkyl or phenalkenyl of up to ten carbon atoms, which may be substituted on the ring by from one to three substitutents selected from halogen, methyl, methoxy, nitro, amino, mono- and dialkylamino, and mono- and dialkylaminocarbonyl wherein each alkyl moiety contains from one to four carbon atoms;

$R^3$ is (a) one of the moieties represented by $R^2$ or is (b) a moiety 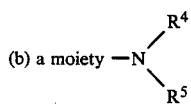

wherein $R^4$ is alkyl of one to four carbon atoms, phenyl, or phenalkyl of up to ten carbon atoms, $R^5$ is hydrogen or one of the moieties represented by $R^4$, or $R^4$ and $R^5$ together with the interjacent nitrogen atom represent 1-piperidino, 2-(ethoxycarbonyl)-1-piperidino, or 4-morpholino.

In these compounds, each alkyl, alkenyl, alkylene and alkenylene (as in phenalkyl and phenalkenyl) moiety may be straight-chain or branched-chain.

Compounds of Formula I can be prepared by treating a phosphonothioic or phosphonodithioic chloride of the formula:

 (II)

with an alkali metal salt of a sulfonamide of the formula

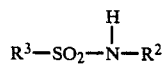 (III)

The treatment of the chloride (II) with a salt of the sulfonamide (III) is effected by adding the chloride at a controlled rate to a solution of the salt in an inert solvent, at a low temperature—for example, 0° C.-5° C.—moisture being excluded, then warming the mixture to room temperature, or somewhat above. Preferably, the chloride is added as a solution in the same solvent in which the salt is dissolved. Suitable as the solvent are organic materials such as ether and tetrahydrofuran, or acetonitrile. The product is isolated and purified by conventional procedures, as shown in the examples, hereinafter.

As is shown in U.S. Pat. No. 4,390,929, and in U.S. Pat. No. 4,190,652, the phosphonodithioic chloride precursor (II, X is sulfur) can be prepared by treating a phosphonothioic dichloride of the formula

 (IV)

with an appropriate thiol, $R^1$-SH, in the presence of a solvent and an amine base, as hydrogen halide acceptor. Aromatic hydrocarbons, such as toluene, are suitable as the solvent. Any tertiary amine base is suitable, but the trialkylamines appear to be most suitable. Water should be excluded from the reaction mixture—as by using anhydrous reagents and conducting the treatment under nitrogen. Isolation of the product is effected by conventional techniques.

The phosphonothioic chloride precursor (II, X is oxygen) can be prepared by a method analogous to that described in U.S. Pat. No. 4,190,652 for preparing the corresponding phosphonodithioic chloride—i.e., by treating a phosphonic dichloride of the formula

 (V)

with an appropriate thiol, $R^1$-SH, in the presence of an inert solvent and an amine base as hydrogen chloride acceptor. Aromatic hydrocarbons, such as toluene, are suitable as the solvent. Any tertiary amine base is suitable, but the trialkylamines appear to be most suitable. Water should be excluded from the reaction mixture—as by using anhydrous reagents and conducting the treatment under nitrogen. Isolation of the product is effected by conventional techniques.

The phosphonothioic chloride (II, X is oxygen) also can be prepared by the method described by A. A. Neimysheva, et al., Journal of General Chemistry, U.S.S.R. (English), 1966, volume 36, pages 520–525—i.e., by slowly adding an appropriate sulfenyl chloride

 (VI)

to a stirred solution of the appropriate phosphonous dichloride of the formula

 (VII)

in sulfur dioxide at a low temperature—e.g., −15° C. to −60° C.—then warming the resulting mixture to room temperature, stripping it of volatiles and vacuum distilling the residue to give the product.

Those phosphonothioic chlorides (II, X is oxygen) wherein $R^1$ is alkyl also can be prepared by treating a S,S—di—$R^1$ R-phosphonodithioate of the formula

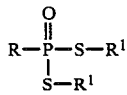
(VIII)

wherein both of $R^1$ are the same, with a chlorinating agent selected from sulfuryl chloride and chlorine. Suitably, the treatment is conducted by adding the chlorinating agent to a stirred solution of the dithioate in an inert solvent, at a temperature of about 0°–10° C. Suitable solvents are the haloalkanes, such as methylene dichloride and carbon tetrachloride. Water should be excluded from the reaction mixture—as by using anhydrous reagents and conducting the treatment under nitrogen—i.e., in a nitrogen atmosphere. Preferably a slight stoichiometric excess—up to about 10% excess—of the chlorinating agent is used, relative to the dithioate. Isolation and purification of the product is accomplished by conventional techniques. In many cases, the by-product $R^1$-sulfenyl chloride is a low-boiling material that is easily removed by evaporation techniques.

The dithioate precursors (formula VIII) can be prepared by known methods. Conveniently, they can be prepared by treating the appropriate alkylphosphonous dichloride (VII) in an inert solvent, with two equivalents of the appropriate thiol, $R^1$-SH, either in the form of its alkyl metal salt, or in the presence of two equivalents of a hydrogen chloride acceptor.

The sulfonamide precursors (III) as a class are known compounds, and the alkali metal salts thereof are prepared by conventional methods and techniques, as is demonstrated in the Examples, hereinafter. Those of the class that are novel are readily prepared by conventional methods, as by treating the appropriate sulfonyl halide, $R^3$—$SO_2$—halogen, with the appropriate amine, $R^2NH_2$. Compounds of Formula III wherein $R^3=-NR^4R^5$ are prepared; a method for their preparation is described by G. Weisz and G. Schulze, Annalen Der Chemie, volume 729, pages 40–51 (1969).

The preparation and isolation of particular individual species of the genus of Formula I are described in the Examples, hereinafter. Other typical individual species are the following, each identified in terms of the symbols in Formula I, in all cases X being oxygen:

| Species | R | $R^1$ | $R^2$ | $R^3$ |
|---|---|---|---|---|
| A | methyl | propyl | methyl | 1-piperidino |
| B | ethyl | 1-methyl-propyl | methyl | 1-piperidino |
| C | ethyl | propyl | methyl | 4-morpholino |
| D | methyl | 1-methyl-propyl | methyl | 4-morpholino |
| E | methyl | propyl | methyl | di-(n-butyl)amino |
| F | ethyl | 1-methyl-propyl | methyl | di-(n-butyl)amino |
| G | ethyl | propyl | methyl | (methyl)(phenyl)amino |
| H | methyl | 1-methyl-propyl | methyl | (methyl)(phenyl)amino |
| I | ethyl | propyl | propargyl | methyl |
| J | methyl | 1-methyl-propyl | propargyl | methyl |
| K | methyl | propyl | propargyl | dimethylamino |
| L | ethyl | 1-methyl-propyl | propargyl | dimethylamino |
| M | methyl | propyl | methyl | 2-(ethoxycarbonyl)-1-piperidino |
| N | ethyl | 1-methyl-propyl | methyl | 2-(ethoxycarbonyl)-1-piperidino |

The preparation, isolation and testing of individual species of the genus of Formula I, in particular instances, are described in the following examples. In each case, the identity of each of the products, and each of the precursors, was confirmed as necessary by appropriate chemical and spectral analyses.

EXAMPLE 1

S-(1-methylpropyl) P-ethyl N-methyl-N-(methylsulfonyl)-phosphonamidothioate (1)

Under nitrogen, 30.7 ml of triethylamine was added over 10 minutes to a stirred mixture of 14.7 g of ethylphosphonic dichloride, 23.9 ml of 2-butanethiol and 125 ml of dry toluene at 5°–10° C. The resulting mixture was stirred at 5° C. for 2 hours, then at room temperature for 15 hours, diluted with ether and filtered. The filtrate was washed with water, dried ($Na_2SO_4$) and stripped of solvent. Hexane was added to the residue, and the mixture was washed with dilute aqueous bicarbonate solution, then with water, dried ($Na_2SO_4$) and stripped of solvent. The residue was distilled in a Kugelrohr apparatus to give S,S-bis(1-methylpropyl)ethylphosphonodithioate (1A).

Under nitrogen, a solution of 1.64 ml of sulfuryl chloride in 10 ml of carbon tetrachloride was added drop-by-drop over 36 minutes to a stirred solution of 5.09 g of 1A in 40 ml of carbon tetrachloride at 0° C. The resulting mixture was stirred at 0° C. for 7 minutes, for 1.5 hours at 5° C., then stripped of solvent under very low pressure, and the residue was distilled in a Kugelrohr apparatus to give S-(1-methylpropyl)ethylphosphonochloridothioate (1B), as a colorless liquid, b.p.: 70° C., 0.005 Torr.

7.55 g of methylamine was added over one hour to a stirred mixture of 11.4 g of methanesulfonyl chloride and 50 ml of ether at 5° C. The resulting mixture was stirred at 5° C. for one hour, for 15 hours at room temperature, then filtered. The filtrate was dried ($MgSO_4$) and stripped of solvent, to give N-methyl methanesulfonamide (1C), as a yellow liquid.

0.12 g of sodium hydride was added to a stirred mixture of 0.54 g of 1C and 10 ml of ether, at 5° C. under nitrogen. The resulting mixture was stirred at room temperature for one hour, cooled to 5° C. and a solution of 1 g of 1B in 3 ml of ether was added drop-by-drop, at 5°–10° C. The mixture was stirred for 2.5 hours at 5° C., at room temperature for 24 hours, then 3 ml of tetrahydrofuran was added and the mixture was stirred for 16 hours. Then the mixture was diluted with methylene chloride, and washed with water, and the organic phase was dried ($Na_2SO_4$) and the solvent was evaporated. The residue was vacuum-chromatographed over silica gel, using ether as eluent, to give 1, as an amber liquid.

EXAMPLE 2

S-propyl P-ethyl N-(ethylsulfonyl)-N-methylphosphonamidothioate (2)

41.0 g of sulfuryl chloride was added drop-by-drop to 25.5 ml of 1-propanethiol, with stirring, at 0° C., under nitrogen. After 15 minutes, the mixture was added drop-by-drop (over 45 minutes) to 40.62 g of ethylphosphonous dichloride and 60 ml of sulfur dioxide at −70° C. under nitrogen. After 20 minutes the mixture was allowed to warm to room temperature and the solvent was evaporated. The residue was distilled in a Kugelrohr apparatus to give S-propyl ethylphosphonochloridothioate (2A) as a colorless liquid, b.p.: 95° C., 0.30 Torr.

2 was prepared as a yellow liquid, by treating 2A with N-methyl ethanesulfonamide (prepared from ethylsulfonyl chloride and methylamine, according to the procedure described for preparing 1C from methylsulfonyl chloride and methylamine), according to the procedure described in Example 1 for preparing 1 from 1B and 1C.

EXAMPLES 3 TO 138

The following additional individual species of the genus of Formula I, each identified in terms of the symbols used in Formula I, in all cases X being oxygen, were prepared from the appropriate reagents by the procedures described in Examples 1 and 2.

TABLE I

| Example No. | Compound No. | R | $R^1$ | $R^2$ | $R^3$ | Physical State |
|---|---|---|---|---|---|---|
| 3 | 3 | ethyl | propyl | methyl | methyl | Amber liquid |
| 4 | 4 | ethyl | 1-methylpropyl | methyl | phenyl | Yellow liquid |
| 5 | 5 | ethyl | propyl | methyl | phenyl | Yellow liquid |
| 6 | 6 | ethyl | 1-methylpropyl | methyl | 4-methylphenyl | Amber liquid |
| 7 | 7 | ethyl | propyl | methyl | 4-methylphenyl | Amber liquid |
| 8 | 8 | ethyl | 1-methylpropyl | methyl | phenyl | Amber liquid |
| 9 | 9 | ethyl | 1-methylpropyl | methyl | 4-chlorophenyl | Amber liquid |
| 10 | 10 | ethyl | 1-methylpropyl | 1-methylethyl | phenyl | Amber liquid |
| 11 | 11 | ethyl | 1-methylpropyl | benzyl | phenyl | Yellow liquid |
| 12 | 12 | ethyl | 1-methylpropyl | methyl | styryl | Yellow liquid |
| 13 | 13 | ethyl | 1-methylpropyl | methyl | 2,4,6-trimethylphenyl | Amber liquid |
| 14 | 14 | ethyl | 1-methylpropyl | methyl | 2,5-dichlorophenyl | White solid, m.p.: 90–96° C. |
| 15 | 15 | ethyl | 1-methylpropyl | methyl | 4-bromophenyl | Yellow liquid |
| 16 | 16 | ethyl | 1-methylpropyl | methyl | 2-nitrophenyl | Amber liquid |
| 17 | 17 | ethyl | 1-methylpropyl | methyl | 1-methylethyl | Pale yellow liquid |
| 18 | 18 | ethyl | propyl | methyl | chloromethyl | Yellow liquid |
| 19 | 19 | ethyl | propyl | methyl | butyl | Pale yellow liquid |
| 20 | 20 | ethyl | propyl | methyl | 3-chloropropyl | Yellow liquid |
| 21 | 21 | ethyl | propyl | methyl | 1-methylethyl | Yellow liquid |
| 22 | 22 | ethyl | 1-methylpropyl | phenyl | phenyl | Yellow liquid |
| 23 | 23 | ethyl | 1-methylpropyl | methyl | 1-naphthyl | Yellow liquid |
| 24 | 24 | ethyl | 1-methylpropyl | methyl | 2,4,5-trichlorophenyl | Amber liquid |
| 25 | 25 | ethyl | 1-methylpropyl | methyl | 4-nitrophenyl | Amber liquid |
| 26 | 26 | ethyl | 1-methylpropyl | methyl | 4-methoxyphenyl | Yellow liquid |
| 27 | 27 | ethyl | propyl | methyl | 2-naphthyl | Yellow liquid |
| 28 | 28 | ethyl | propyl | methyl | 2,4,6-trimethylphenyl | Yellow liquid |
| 29 | 29 | ethyl | propyl | methyl | 1-naphthyl | Yellow liquid |
| 30 | 30 | ethyl | propyl | methyl | 2,4,5-trichlorophenyl | Yellow liquid |
| 31 | 31 | ethyl | propyl | methyl | 2,5-dichlorophenyl | White solid m.p.: 81.5–85.5 |
| 32 | 32 | ethyl | propyl | methyl | 2-nitrophenyl | Yellow liquid |
| 33 | 33 | ethyl | propyl | methyl | 4-bromophenyl | Yellow liquid |
| 34 | 34 | ethyl | propyl | methyl | 4-nitrophenyl | Yellow liquid |
| 35 | 35 | ethyl | propyl | methyl | 4-methoxyphenyl | Yellow liquid |
| 36 | 36 | ethyl | 1-methylpropyl | methyl | chloromethyl | Yellow liquid |
| 37 | 37 | ethyl | 1-methylpropyl | methyl | 3-chloropropyl | Yellow liquid |
| 38 | 38 | ethyl | 1-methylpropyl | methyl | butyl | Pale yellow liquid |
| 49 | 39 | ethyl | 1-methylpropyl | methyl | ethyl | Yellow liquid |
| 40 | 40 | ethyl | 1-methylpropyl | methyl | 4-chlorophenyl | Yellow liquid |
| 41 | 41 | ethyl | propyl | methyl | benzyl | Yellow liquid |
| 42 | 42 | ethyl | propyl | methyl | styryl | Yellow liquid |
| 43 | 43 | ethyl | butyl | methyl | 1-methylethyl | Colorless liquid |
| 44 | 44 | methyl | propyl | methyl | 1-methylethyl | Yellow liquid |

TABLE I-continued

| Example No. | Compound No. | R | R¹ | R² | R³ | Physical State |
|---|---|---|---|---|---|---|
| 45 | 45 | methyl | 1-methylpropyl | methyl | 2-naphthyl | Yellow liquid |
| 46 | 46 | ethyl | propyl | methyl | phenyl | Yellow liquid |
| 47 | 47 | ethyl | 2-methylpropyl | methyl | 1-methylethyl | Pale yellow liquid |
| 48 | 48 | ethyl | 2-methylpropyl | methyl | 3-chlorophenyl | Pale yellow liquid |
| 49 | 49 | ethyl | 2-methylpropyl | methyl | ethyl | Pale yellow liquid |
| 50 | 50 | ethyl | hexyl | methyl | 1-methylethyl | Colorless liquid |
| 51 | 51 | ethyl | 2-methylpropyl | methyl | butyl | Pale yellow liquid |
| 52 | 52 | ethyl | 2-methylpropyl | methyl | 2-chlorophenyl | Colorless liquid |
| 53 | 53 | ethyl | 1,1-dimethylethyl | methyl | ethyl | Pale yellow liquid |
| 54 | 54 | ethyl | 1,1-dimethylethyl | methyl | 3-chloropropyl | Pale yellow liquid |
| 55 | 55 | ethyl | 1,1-dimethylethyl | methyl | 1-methylethyl | Yellow liquid |
| 56 | 56 | ethyl | 1,1-dimethylethyl | methyl | chloromethyl | Colorless liquid |
| 57 | 57 | ethyl | propyl | methyl | dichloromethyl | Yellow liquid |
| 58 | 58 | ethyl | 1-methylpropyl | methyl | dichloromethyl | Yellow liquid |
| 59 | 59 | ethyl | propyl | methyl | propyl | Pale yellow liquid |
| 60 | 60 | ethyl | propyl | 1-methylethyl | phenyl | Yellow liquid |
| 61 | 61 | ethyl | propyl | methyl | phenyl | Yellow liquid |
| 62 | 62 | ethyl | 1-methylpropyl | methyl | 4-fluorophenyl | Amber liquid |
| 63 | 63 | ethyl | 1-methylpropyl | methyl | 4-iodophenyl | Amber liquid |
| 64 | 64 | ethyl | 1-methylpropyl | methyl | 3-nitrophenyl | Amber liquid |
| 65 | 65 | ethyl | 1-methylpropyl | methyl | 2-aminophenyl | Amber liquid |
| 66 | 66 | ethyl | 1,1-dimethylpropyl | methyl | methyl | Pale yellow liquid |
| 67 | 67 | ethyl | 1,1-dimethylpropyl | methyl | 1-methylethyl | Pale yellow liquid |
| 68 | 68 | ethyl | propyl | methyl | octyl | Pale yellow liquid |
| 69 | 69 | methyl | propyl | methyl | ethyl | Pale yellow liquid |
| 70 | 70 | methyl | 1-methylpropyl | methyl | ethyl | Pale yellow liquid |
| 71 | 71 | ethyl | 1-methylpropyl | methyl | 2-thienyl | Amber liquid |
| 72 | 72 | methyl | propyl | methyl | propyl | Pale yellow liquid |
| 73 | 73 | methyl | propyl | methyl | octyl | Pale yellow liquid |
| 74 | 74 | methyl | 1-methylpropyl | methyl | octyl | Pale yellow liquid |
| 75 | 75 | methyl | propyl | methyl | chloromethyl | Pale yellow liquid |
| 76 | 76 | methyl | 1-methylpropyl | methyl | propyl | Yellow liquid |
| 77 | 77 | methyl | propyl | methyl | 3-chloropropyl | Pale yellow liquid |
| 78 | 78 | methyl | 1-methylpropyl | methyl | 3-chloropropyl | Yellow liquid |
| 79 | 79 | methyl | 1-methylpropyl | methyl | chloromethyl | Pale yellow liquid |
| 80 | 80 | ethyl | 1-methylpropyl | methyl | 2,4-dinitrophenyl | Amber liquid |
| 81 | 81 | ethyl | 1-methylpropyl | methyl | 4-(methylamino)-3-nitrophenyl | Yellow liquid |
| 82 | 82 | ethyl | 1-methylpropyl | methyl | 2,4,6-trimethylphenyl | Yellow liquid |
| 83 | 83 | ethyl | 1-methylpropyl | methyl | 3-(methylaminocarbonyl)phenyl | Yellow gel |
| 84 | 84 | ethyl | propyl | methyl | 4-iodophenyl | Yellow liquid |
| 85 | 85 | ethyl | propyl | methyl | 4-fluorophenyl | Yellow liquid |
| 86 | 86 | methyl | propyl | methyl | butyl | Yellow liquid |
| 87 | 87 | methyl | 1-methylpropyl | methyl | butyl | Pale yellow liquid |
| 88 | 88 | methyl | 1-methylpropyl | methyl | 1-methylethyl | Yellow liquid |
| 89 | 89 | methyl | propyl | methyl | methyl | Pale yellow liquid |
| 90 | 90 | methyl | 1-methylpropyl | methyl | methyl | Pale yellow liquid |
| 91 | 91 | ethyl | 1-methylpropyl | methyl | propyl | Pale yellow liquid |
| 92 | 92 | ethyl | 1,1-dimethylethyl | methyl | methyl | Pale yellow liquid |
| 93 | 93 | ethyl | propyl | methyl | 2,4-dinitrophenyl | Yellow liquid |
| 94 | 94 | ethyl | propyl | methyl | 4-(methylamino)-2-nitrophenyl | Yellow liquid |
| 95 | 95 | ethyl | propyl | methyl | 2-aminophenyl | Amber liquid |
| 96 | 96 | ethyl | propyl | methyl | 2-thienyl | Yellow liquid |
| 97 | 97 | ethyl | 1,1-dimethylethyl | methyl | propyl | Pale yellow liquid |
| 98 | 98 | ethyl | 1-methylpropyl | methyl | propyl | Pale yellow liquid |
| 99 | 99 | ethyl | propyl | methyl | 4-fluorophenyl | Yellow liquid |
| 100 | 100 | ethyl | propyl | methyl | 2,4,6-trimethylphenyl | Yellow liquid |
| 101 | 101 | ethyl | 2-methylpropyl | methyl | methyl | Very pale yellow liquid |
| 102 | 102 | ethyl | 2-methylpropyl | methyl* | octyl | Pale yellow liquid |

TABLE I-continued

| Example No. | Compound No. | R | R¹ | R² | R³ | Physical State |
|---|---|---|---|---|---|---|
| 103 | 103 | methyl | propyl | methyl | 2-methyl-2-propenyl | Very pale yellow liquid |
| 104 | 104 | methyl | 1-methylpropyl | methyl | 2-methyl-2-propenyl | Very pale yellow liquid |
| 105 | 105 | ethyl | 1-methylpropyl | methyl | 2-methyl-2-propenyl | Pale yellow liquid |
| 106 | 106 | ethyl | propyl | methyl | 3-(methylaminocarbonyl)phenyl | Colorless liquid |
| 107 | 107 | ethyl | 1-methylpropyl | methyl | 3-pyridyl | Amber liquid |
| 108 | 108 | ethyl | propyl | methyl | 3-pyridyl | Amber liquid |
| 109 | 109 | methyl | propyl | methyl | phenyl | Amber liquid |
| 110 | 110 | methyl | 1-methylpropyl | methyl | phenyl | Yellow liquid |
| 111 | 111 | methyl | propyl | methyl | 4-bromophenyl | Yellow liquid |
| 112 | 112 | methyl | 1-methylpropyl | methyl | 4-bromophenyl | Yellow liquid |
| 113 | 113 | methyl | propyl | ethyl | methyl | Pale yellow liquid |
| 114 | 114 | methyl | 1-methylpropyl | ethyl | ethyl | Yellow liquid |
| 115 | 115 | methyl | propyl | ethyl | ethyl | Very pale yellow liquid |
| 116 | 116 | methyl | 1-methylpropyl | ethyl | methyl | Pale yellow liquid |
| 117 | 117 | methyl | 1-methylpropyl | methyl | methyl | Pale yellow liquid |
| 118 | 118 | methyl | 1,1-dimethylethyl | methyl | 3-chloropropyl | Pale yellow liquid |
| 119 | 119 | methyl | 1,1-dimethylethyl | methyl | methyl | Yellow liquid |
| 120 | 120 | methyl | 1,1-dimethylethyl | methyl | propyl | Pale yellow liquid |
| 121 | 121 | methyl | 1-methylpropyl | ethyl | 1-methylethyl | Yellow liquid |
| 122 | 122 | methyl | 1-methylpropyl | propyl | 1-methylethyl | Yellow liquid |
| 123 | 123 | methyl | 1-methylpropyl | propyl | ethyl | Pale yellow liquid |
| 124 | 124 | ethyl | propyl | methyl | 2-methyl-2-propenyl | Pale yellow liquid |
| 125 | 125 | methyl | 1,1-dimethylpropyl | methyl | 1-methylethyl | Yellow liquid |
| 126 | 126 | methyl | propyl | propyl | methyl | Yellow liquid |
| 127 | 127 | methyl | propyl | propyl | ethyl | Yellow liquid |
| 128 | 128 | methyl | 2-methylpropyl | methyl | methyl | Yellow liquid |
| 129 | 129 | methyl | 2-methylpropyl | methyl | propyl | Yellow liquid |
| 130 | 130 | ethyl | 1,1-dimethylethyl | methyl | butyl | Pale yellow liquid |
| 131 | 131 | methyl | propyl | ethyl | 1-methylethyl | Yellow liquid |
| 132 | 132 | methyl | 2-methylpropyl | methyl | 1-methylethyl | Yellow liquid |
| 133 | 133 | methyl | 1-methylpropyl | methyl | octyl | Pale yellow liquid |
| 134 | 134 | methyl | propyl | methyl | 3-(ethylthio)propyl | Yellow liquid |
| 135 | 135 | methyl | 1-methylpropyl | methyl | 3-(ethylthio)propyl | Pale yellow liquid |
| 136 | 136 | methyl | 1-methylpropyl | ethyl | 3-chloropropyl | Yellow liquid |
| 137 | 137 | ethyl | propyl | methyl | 3-(ethylthio)propyl | Yellow liquid |
| 138 | 138 | ethyl | 1-methylpropyl | methyl | 3-(ethylthio)propyl | Yellow liquid |

EXAMPLE 139

S-1,1-dimethylpropyl N,P-dimethyl-N-((1-methylethyl)sulfonyl)phosphonamidodithioate (139)

At about 0° C., 17.05 g of 40% methylamine in water was added drop-by-drop to a solution of 14.25 g of 1-methylethanesulfonyl chloride in 30 ml of methylene chloride. Then the mixture was allowed to warm to room temperature, held for 2 hours, and diluted with water. The organic phase was separated, dried (Na₂SO₄) and stripped of solvent to give N,1-dimethylethanesulfonamide (139A), as an amber liquid.

26.85 g of methylphosphonothioic dichloride and 18.5 ml of 1,1-dimethylpropanethiol were mixed with 25 ml of dry toluene under nitrogen. Then 15.15 g of triethylamine was added drop-by-drop to the mixture over 45 minutes, the temperature of the mixture being allowed to rise to 38° C. The mixture was filtered, and the solvent was stripped from the filtrate. The residue was slurried in ether, the slurry was filtered, and the filtrate was stripped of solvent. The residue was distilled under reduced pressure in a Kugelrohr apparatus to give 1,1-dimethylpropyl methylphosphonochloridodithioate (139B), b.p.: 70° C. at 0.03 Torr.

A solution of 0.95 g of 139A in 1 ml of dry THF was added drop-by-drop to a suspension of 0.37 g of sodium hydride in 4 ml of dry THF, under nitrogen, at 0° C. The mixture was allowed to warm to room temperature, then after 30 minutes was cooled to 0° C. and a solution of 1.5 g of 139B in 2 ml of dry THF was added drop-by-drop. The mixture was allowed to warm to room temperature and after 3 hours and 40 minutes was filtered. The solvent was stripped from the filtrate. The residue was flash chromatographed over silica gel using a 1.5:8.5 v:v mixture of ethyl acetate and a hexane as eluent, to give 139, as a yellow liquid.

EXAMPLE 140

S-1-methylpropyl P-ethyl-N-methyl-N-(phenylsulfonyl)phosphonamidodithioate (140)

With stirring at 5° C., 6.8 g of 40% methylamine in water was added over 45 minutes to 17.7 g of a mixture of benzenesulfonyl chloride and 50 ml of dry THF. Then the mixture was stirred at room temperature for 5.5 hours, diluted with methylene chloride and filtered. The filtrate was washed with water, dried ($Na_2SO_4$) and stripped of solvent. The residue was dissolved in methylene chloride, the solution was washed with water, dried and stripped of solvent to give N-methyl-benzenesulfonamide (140A), as a yellow liquid.

At 5° C., under nitrogen, 34.8 ml of triethylamine was added drop-by-drop over 10 minutes to a stirred mixture of 40.75 g of ethylphosphonothioic dichloride and 22.5 g of 2-butanethiol. The resulting mixture was stirred at room temperature for 21 hours, diluted with ether, filtered, and the solvent was stripped from the filtrate. The residue was distilled in a Kugelrohr apparatus to give 1-methylpropyl ethylphosphonochloridodithioate (140B), as a yellow liquid, b.p.: 90° C., 0.003 Torr.

At 5° C., under nitrogen, 1.2 g of potassium tertiary-butoxide was added to a stirred solution of 1.7 g of 140A in 30 ml of acetonitrile. The mixture was stirred at room temperature for one hour, a solution of 2.25 g of 140B in 6 ml of acetonitrile was added drop-by-drop, the mixture was stirred for 3 hours and then refluxed for 4 days. The mixture was diluted with methylene chloride, washed with water, dried ($Na_2SO_4$) was stripped of solvent. The residue was vacuum-chromatographed on silica gel, using a 9:1 v:v mixture of methylene chloride and ether as eluent. The entire product was re-chromatographed over silica gel using a 1:1 v:v mixture of methylene chloride and hexane, to give 140, as a yellow liquid.

EXAMPLES 141 TO 144

The following additional individual species of the genus of Formula I, each identified in terms of the symbols used in Formula I, X being sulfur in all cases, were prepared from the appropriate reagents by the procedures described in Examples 139 and 140.

TABLE II

| Example No. | Compound No. | R | $R^1$ | $R^2$ | $R^3$ | Physical State |
|---|---|---|---|---|---|---|
| 141 | 141 | methyl | 1-methyl-propyl | methyl | 1-methyl-ethyl | colorless liquid |
| 142 | 142 | ethyl | 1-methyl-propyl | methyl | 1-methyl-ethyl | colorless liquid |
| 143 | 143 | ethyl | propyl | methyl | 1-methyl-ethyl | colorless liquid |

EXAMPLE 144

S-(1-methylpropyl) P-ethyl-N-(dimethylaminosulfonyl)-N-methylphosphonamidothioate (144)

At 5° C., 6.8 g of a 40% solution of methylamine in water was added over 12 minutes to a stirred mixture of 14.3 g of dimethylsulfamoyl chloride and 50 ml of methylene chloride, and the mixture was stirred at room temperature for 24 hours. The organic phase was separated, washed with water, dried ($MgSO_4$) and stripped of solvent, to give trimethylsulfamide (144A), as a colorless liquid.

At 5° C., under nitrogen, 0.24 g of sodium hydride was added to a stirred solution of 0.69 g of 144A in 15 ml of THF, then a solution of 1.1 g of 1B in 3 ml of THF was added drop-by-drop over 2 minutes. The mixture was stirred a room temperature for 5 days, diluted with methylene chloride, washed with water, dried ($Na_2SO_4$) and stripped of solvent. The residue was vacuum chromatographed over silica gel, using a 9:1 v:v mixture of methylene chloride and ether as eluent, to give 144, as a yellow liquid.

EXAMPLES 145-147

The following additional individual species of the genus of Formula I, each identified in terms of the symbols used in Formula I, X being oxygen and $R^3$ being dimethylamino, in all cases, were prepared from the appropriate reagents by the procedures described in Example 141.

TABLE III

| Example No. | Compound No. | R | $R^1$ | $R^2$ | Physical State |
|---|---|---|---|---|---|
| 145 | 145 | ethyl | propyl | methyl | yellow liquid |
| 146 | 146 | methyl | propyl | methyl | amber liquid |
| 147 | 147 | methyl | 1-methyl-propyl | methyl | amber liquid |

Compounds of the invention have been found to be toxic with respect to invertebrate pests, by which is meant insects of the class Insecta and related classes of arthropods, such as the acarids (e.g., mites), ticks, spiders, wood lice and the like. In particular, they have been found to be highly toxic to mites. Further, it has been found that compounds of the invention act systemically—that is, when applied to the plant, a compound of the invention penetrates into the cells and vascular system of the plant and is translocated therein and thereby disseminated throughout the plant without injury to the plant, yet effectively kills insects that chew upon tissues of the plant or suck juices from the plant. Some of the compounds act upon the insects very rapidly—i.e., they are "quick-knockdown agents", even though they may not be very toxic to the insects.

For application, a compound of the invention ordinarily is applied most effectively by formulating it with a suitable inert carrier or surface-active agent, or both. The invention, therefore, also includes compositions suitable for combatting pests, such compositions comprising an inert carrier or surface-active agent, or both, and as active ingredient at least one compound of the invention. The invention also provides a method of combatting pests at a locus, which comprises applying to that locus a compound of the invention or a pesticidal composition according to the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides—i.e., horticulturally acceptable adjuvants—are suitable.

Suitable solid carriers are natural and synthetic clays and silicates, for example, natural silicas such as diatomaceous earths; magnesium silicates, for example, talcs; magnesium aluminum silicates, for example, attapulgites are vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25-75% by weight of active compound and usually contain, in addition to the solid carrier, 3-10% by weight of a dispersing agent, 2-15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676–0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3-7% by weight of a blend of surfactants, which act as wetting, dispersing, suspending and binding agents, and 1-3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control pests comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

Activity of compounds of the invention with respect to insect and acarine pests was determined by using standardized test methods to measure the toxicity of the compounds as follows:

I. Houseflies (*Musca domestica* (Linne)) were tested by placing 50 4- to 5-day old adult houseflies into a spray cage and spraying with 0.6 ml of a solution of test compound. After spraying, the flies were observed to ascertain any knockdown effect, and then were anesthetized with $CO_2$ and transferred to a recovery cage containing a milk pad for food. The cages were held for 18–20 hours after which mortality counts were made. Both dead and moribund flies were counted. The tests were conducted employing several different dosage rates for each test compound.

II. Pea aphids (*Acyrthosiphon pisum* (Harris)) were tested by placing about 100 adult aphids on broad bean plants. The plants were sprayed with dilutions of an acetone solution of the test compound in water containing an emulsifier and held under laboratory conditions for 18 to 20 hours, at which time the living aphids on the plants were counted. The tests were conducted employing several different dosage rates for each test compound.

III. Adult female two-spotted spider mites (*Tetranychus urticae* (Koch)) were tested by placing 50–75 mites on the bottom side of leaves of pinto bean plants. The leaves were sprayed with dilutions of an acetone solution of the test compound in water containing an emulsifier and kept under laboratory conditions for about 20 hours, at which time mortality counts were made. The tests were conducted employing several different dosage rates for each compound.

IV. Third instar corn earworm larvae (*Heliothis zea* (Boddie)) were tested by spraying broad bean plants with dilutions of an acetone solution of the test compound in water containing an emulsifier. Immediately after spraying, 5 larvae were transferred to the plant and held for 44–46 hours, at which time the dead and moribund larvae were counted. The tests were conducted employing several different dosage rates for each test compound.

In each set of tests, identical tests were conducted using parathion as a standard for comparison.

In each instance, the toxicity of the test compound was compared to that of a standard pesticide, parathion, the relative toxicity of the test compound then being expressed in terms of the relationship between the amount of the test compound and the amount of the standard pesticide required to produce the same percentage (50%) of mortality in the test insects. By assigning the standard pesticide an arbitrary rating of 100, the toxicity of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 would be twice as active, as the standard pesticide. The results are set forth in Table IV.

TABLE IV

| Compound Number | Toxicity Index | | | |
|---|---|---|---|---|
| | Housefly | Pea Aphid | Corn Earworm | Spider Mite |
| 1 | 30K[a] | 30K | 30 | 2100 |
| 2 | 25K | 20K | 60 | 2300 |
| 3 | 40K | 10K | 35 | 2400 |
| 4 | 30K | 25K | 10 | 12000 |
| 5 | 10K | 10 | 55 | 3200 |
| 6 | 10 | 20K | 0 | 520 |
| 7 | 0 | 10K | 0 | 370 |
| 8 | 30K | 100 | 15 | 3800 |
| 9 | 30K | 70 | 45 | 2600 |
| 10 | 25K | 30K | 20 | 1500 |
| 11 | 30K | 150K | 10 | 850 |
| 12 | 15K | 50K | 20 | 1000 |
| 13 | 10K | 35K | 10 | 470 |
| 14 | 15K | 25K | 10 | 2300 |
| 15 | 15K | 25K | 10 | 17500 |
| 16 | 30K | 25K | 10 | 650 |
| 17 | 25K | 30 | 40 | 1400 |
| 18 | 30K | 25K | 15 | 3500 |
| 19 | 20K | 10K | 5 | 4100 |
| 20 | 20K | 15 | 10 | 5000 |
| 21 | 15K | 10 | 15 | 7000 |
| 22 | 10K | 15K | 10 | 1000 |
| 23 | <5K | 15K | 5 | 1100 |
| 24 | <5K | 15K | 10 | 500 |
| 25 | 5K | 5K | 5 | 750 |
| 26 | 10K | 35K | 0 | 750 |
| 27 | 0 | 5 | 0 | 440 |
| 28 | 0 | 5 | 0 | 50 |
| 29 | 0 | 5 | 0 | 460 |
| 30 | <5 | 5 | 0 | 800 |
| 31 | <5K | 5 | 0 | 5100 |
| 32 | 10K | <5K | 0 | 540 |
| 33 | <5 | 5K | 10 | 2400 |
| 34 | <5 | <5 | 0 | 655 |
| 35 | <5 | 5 | 0 | 425 |
| 36 | 20K | 15K | 5 | 2200 |
| 37 | 15K | 25K | 5 | 2200 |
| 38 | 20K | 60 | 5 | 3200 |
| 39 | 20K | 60 | 10 | 2200 |
| 40 | 15K | 20K | 5 | 2900 |
| 41 | 10K | 20 | 15 | 2900 |
| 42 | 5K | 10K | 5 | 1200 |
| 43 | 0 | 5K | 0 | 340 |
| 44 | 10K | 10K | 280 | 4200 |
| 45 | <5K | 10K | 10 | 900 |
| 46 | <5K | 5K | 5 | 850 |
| 47 | 5K | 10K | 0 | 900 |
| 48 | 5 | 120K | 0 | 1000 |
| 49 | 5K | 60K | 30 | 430 |
| 50 | 0 | <5 | 0 | 45 |
| 51 | 5K | 30K | 0 | 1000 |
| 52 | 15K | 30K | 5 | 4900 |
| 53 | 15K | 45K | 95 | 800 |
| 54 | 5K | 30K | 15 | 2500 |
| 55 | 10K | 45K | 35 | 1000 |
| 56 | 15K | 40K | 35 | 3000 |
| 57 | 5K | 10 | 5 | 3200 |
| 58 | 15K | 20 | 0 | 4600 |
| 59 | 10K | 15 | 65 | 5100 |
| 60 | 0 | 5 | 0 | 1500 |
| 61 | <5 | 5 | 10 | 350 |
| 62 | 15K | 40 | 10 | 4800 |
| 63 | 5K | 30 | 20 | 2800 |

TABLE IV-continued

| Compound Number | Housefly | Pea Aphid | Corn Earworm | Spider Mite |
|---|---|---|---|---|
| 64 | 10K | 10 | 15 | 5100 |
| 65 | 10K | 10 | 0 | 290 |
| 66 | 30K | 90 | 15K | 1200 |
| 67 | 25K | 120 | 15 | 1700 |
| 68 | 0 | 0 | 0 | 5100 |
| 69 | 10K | 20 | 160 | 4500 |
| 70 | 15K | 10 | 160K | 2300 |
| 71 | 10K | 50 | 0 | 2400 |
| 72 | 10K | 35 | 115K | 2400 |
| 73 | 0 | <5 | 0 | 500 |
| 74 | <5K | 45 | 30 | 650 |
| 75 | 10K | 25 | 35K | 2400 |
| 76 | 20K | 85 | 35 | 3800 |
| 77 | 10K | 10 | 20 | 5500 |
| 78 | 10K | 35 | 70 | 5500 |
| 79 | 20K | 130K | 20 | 1800 |
| 80 | <5 | 0 | 0 | 260 |
| 81 | <5 | <5 | <5 | 650 |
| 82 | <5 | <5 | 0 | 650 |
| 83 | <5 | 5 | 0 | 450 |
| 84 | <5K | 5 | 10 | 1700 |
| 85 | <5K | 0 | 10 | 1300 |
| 86 | <5K | 5 | 30 | 1600 |
| 87 | 10K | 20K | 20 | 4300 |
| 88 | 15K | 20K | 40 | 8300 |
| 89 | 15K | 15K | 110 | 1200 |
| 90 | 20K | 20K | 130 | 2300 |
| 91 | 5K | 15K | 0 | 2800 |
| 92 | 15K | 30K | 75 | 1600 |
| 93 | <5 | 0 | 0 | 85 |
| 94 | 0 | 0 | 5 | 460 |
| 95 | 0 | 0 | 0 | 60 |
| 96 | 5 | 10 | 0 | 5300 |
| 97 | 5K | 10 | 25 | 4800 |
| 98 | 10K | 20 | 15 | 7900 |
| 99 | <5 | 5 | 30 | 4800 |
| 100 | 0 | 5 | 0 | 2300 |
| 101 | 10K | 25 | 0 | 3200 |
| 102 | <5K | 10 | 0 | 2700 |
| 103 | <5K | 5 | 10 | 2000 |
| 104 | 5K | 20 | 10 | 1700 |
| 105 | 10K | 40 | 0 | 4100 |
| 106 | <5K | <5 | 0 | 475 |
| 107 | 5K | 20 | 0 | 3000 |
| 108 | 5K | 10 | 10 | 2000 |
| 109 | 5K | 30 | 55 | 3300 |
| 110 | 5 | 75 | 25 | 4300 |
| 111 | 75 | 5 | 20 | 1100 |
| 112 | 5 | 20 | 20 | 1800 |
| 113 | 10 | 20 | 120 | 1700 |
| 114 | 10 | 30 | 70 | 1800 |
| 115 | 5 | 15 | 90 | 2400 |
| 116 | 10 | 120 | 35 | 750 |
| 117 | 10 | 25 | 20 | 1000 |
| 118 | 5 | 60 | 15 | 1600 |
| 119 | 10 | 30 | 20 | 600 |
| 120 | 15 | 120 | 10 | 100 |
| 121 | 10 | 40 | 30 | 750 |
| 122 | 20K | 85K | 30K | 2600 |
| 123 | 20K | 65K | 20K | 5300 |
| 124 | 10K | 25K | <5 | 3300 |
| 125 | 20K | 95K | 30 | 3500 |
| 126 | 20K | 25 | 35 | 1900 |
| 127 | 20K | 40K | 35K | 6200 |
| 128 | 25K | 70K | 100K | 3500 |
| 129 | 20K | 70K | 70K | 2400 |
| 130 | 5K | 30 | 5K | 800 |
| 131 | 10K | 45 | 25K | 1100 |
| 132 | 20K | 50 | 35 | 500 |
| 133 | 5K | 25 | 0 | 1700 |
| 134 | 5K | 30 | 25 | 800 |
| 135 | 20K | 60 | 40 | 1100 |
| 139 | 10K | 30K | 20 | 240 |
| 140 | <5 | 10 | 0 | 280 |
| 141 | 10K | 15K | 30 | 240 |
| 142 | 5K | 60K | 5 | 45 |
| 143 | 5 | 15 | 10 | 430 |
| 144 | 20K | 100 | 20 | 2800 |
| 145 | 5K | 20 | 25 | 1200 |
| 146 | 15 | 60 | 20 | 1100 |
| 147 | 15 | 40 | 80 | 1900 |

[a] K indicates "rapid knockdown"

Additional compounds of this invention are those of Formula I wherein R, $R^1$, $R^2$ and $R^3$ are as defined in Table V.

TABLE V

| Compound No. | R | $R^1$ | $R^2$ | $R^3$ | Physical* State |
|---|---|---|---|---|---|
| 148 | $CH_3$ | n-$C_3H_7$ | $C_2H_5$ | $CH_3$ | P Y L |
| 149 | $CH_3$ | sec-$C_4H_9$ | $C_2H_5$ | $C_2H_5$ | Y L |
| 150 | $CH_3$ | n-$C_3H_7$ | $C_2H_5$ | $C_2H_5$ | P Y L |
| 151 | $CH_3$ | sec-$C_4H_9$ | $C_2H_5$ | $CH_3$ | P Y L |
| 152 | $CH_3$ | sec-$C_4H_9$ | n-$C_3H_7$ | $CH_3$ | P Y L |
| 153 | $CH_3$ | tert-$C_5H_{11}$ | $CH_3$ | 3-chloro-propyl | Y L |
| 154 | $CH_3$ | tert-$C_5H_{11}$ | $CH_3$ | $CH_3$ | Y L |
| 155 | $CH_3$ | tert-$C_5H_{11}$ | $CH_3$ | n-$C_3H_7$ | P Y L |
| 156 | $CH_3$ | sec-$C_4H_9$ | $C_2H_5$ | iso-$C_3H_7$ | Y L |
| 157 | $CH_3$ | sec-$C_4H_9$ | n-$C_3H_7$ | iso-$C_3H_7$ | Y L |
| 158 | $CH_3$ | sec-$C_4H_9$ | n-$C_3H_7$ | $C_2H_5$ | P Y L |
| 159 | $C_2H_5$ | n-$C_3H_7$ | $CH_3$ | 2-methyl-1-propene | P Y L |
| 160 | $CH_3$ | tert-$C_5H_{11}$ | $CH_3$ | iso-$C_3H_7$ | Y L |
| 161 | $CH_3$ | $C_3H_7$ | n-$C_3H_7$ | $CH_3$ | Y L |
| 162 | $CH_3$ | $C_3H_7$ | n-$C_3H_7$ | $C_2H_5$ | Y L |
| 163 | $CH_3$ | iso-$C_4H_9$ | $CH_3$ | $CH_3$ | Y L |
| 164 | $CH_3$ | iso-$C_4H_9$ | $CH_3$ | $C_3H_7$ | Y L |
| 165 | $C_2H_5$ | tert-$C_4H_9$ | $CH_3$ | n-$C_4H_9$ | P Y L |
| 166 | $CH_3$ | n-$C_3H_7$ | $C_2H_5$ | iso-$C_3H_7$ | Y L |
| 167 | $CH_3$ | iso-$C_4H_9$ | $CH_3$ | iso-$C_3H_7$ | Y L |
| 168 | $C_2H_5$ | sec-$C_4H_9$ | $CH_3$ | n-$C_8H_{17}$ | P Y L |
| 169 | $CH_3$ | n-$C_3H_7$ | $CH_3$ | 3-ethylthio-propyl | Y L |
| 170 | $CH_3$ | sec-$C_4H_9$ | $CH_3$ | 3-ethylthio-propyl | P Y L |
| 171 | $C_2H_5$ | tert-$C_4H_9$ | $CH_3$ | phenyl | Y L |
| 172 | $CH_3$ | tert-$C_4H_9$ | $CH_3$ | phenyl | Solid mp 95° to 101° C. |
| 173 | $CH_3$ | sec-$C_4H_9$ | $CH_3$ | 3-chloropropyl | Y L |
| 174 | $C_2H_5$ | n-$C_3H_7$ | $CH_3$ | 3-ethylthiopropyl | Y L |
| 175 | $C_2H_5$ | sec-$C_4H_9$ | $CH_3$ | 3-ethylthiopropyl | Y L |
| 176 | $C_2H_5$ | iso-$C_4H_9$ | $CH_3$ | dimethylamino | Y L |
| 177 | $CH_3$ | tert-$C_4H_9$ | $CH_3$ | dimethylamino | Y L |
| 178 | $CH_3$ | iso-$C_4H_9$ | $CH_3$ | dimethylamino | Y L |
| 179 | $C_2H_5$ | tert-$C_4H_9$ | $CH_3$ | dimethylamino | Y L |
| 180 | $C_2H_5$ | n-$C_3H_7$ | $C_2H_5$ | dimethylamino | Y L |
| 181 | $C_2H_5$ | tert-$C_4H_9$ | $C_2H_5$ | dimethylamino | Y L |
| 182 | $C_2H_5$ | sec-$C_4H_9$ | $C_2H_5$ | dimethylamino | Y L |
| 183 | $C_2H_5$ | sec-$C_4H_9$ | $CH_3$ | 4-morpholino | B L |
| 184 | $C_2H_5$ | sec-$C_4H_9$ | $CH_3$ | piperidino | B L |
| 185 | $CH_3$ | tert-$C_4H_9$ | $C_2H_5$ | dimethylamino | Y L |
| 186 | $CH_3$ | n-$C_3H_7$ | $C_2H_5$ | dimethylamino | Y L |
| 187 | $C_2H_5$ | tert-$C_4H_9$ | $CH_3$ | 4-morpholino | Y L |

TABLE V-continued

| Compound No. | R | $R^1$ | $R^2$ | $R^3$ | Physical* State |
|---|---|---|---|---|---|
| 188 | $CH_3$ | tert-$C_4H_9$ | $CH_3$ | 4-morpholino | Y L |
| 189 | $CH_3$ | iso-$C_4H_9$ | $CH_3$ | 4-morpholino | Y L |
| 190 | $CH_3$ | tert-$C_4H_9$ | $CH_3$ | piperidino | Y L |
| 191 | $CH_3$ | iso-$C_4H_9$ | $CH_3$ | piperidino | Y L |
| 192 | $CH_3$ | tert-$C_5H_{11}$ | $CH_3$ | 4-morpholino | Y L |
| 193 | $CH_3$ | tert-$C_5H_{11}$ | $CH_3$ | piperidino | Y L |
| 194 | $CH_3$ | tert-$C_5H_{11}$ | $CH_3$ | dimethylamino | Y L |
| 195 | $C_2H_5$ | tert-$C_5H_{11}$ | $C_2H_5$ | dimethylamino | Y L |
| 196 | $C_2H_5$ | tert-$C_5H_{11}$ | $CH_3$ | dimethylamino | Y L |

*P Y L = Pale Yellow Liquid
Y L = Yellow Liquid
B L = Brown Liquid

Systemic Activity Tests

Systemic activity of compounds of Formula I was determined as follows:

Mite Tests

The roots of pinto bean plants (*Phaseolus vulgaris*) in the primary leaf stage were placed in a flask containing water plus the test chemical. The stem of the plant was wrapped with non-absorbent cotton fitted snugly into the neck of the flask, to prevent possible fumigant action by the test chemical. Then the plant was infested with 50-100 adult female two-spotted spider mites, held for 48 hours at 85° F., and 50% relative humidity when mortality in the mites was determined visually. A series of different dosages of the test compound in the water were used, and the $LC_{50}$ dosage (the dosage in parts per million by weight of the test chemical in the water required to effect fifty percent kill of the mites) was determined.

Compounds Nos. 1, 2, 3, 5, 17, 18, 19, 21, 26, 36, 37, 39, 44, 48, 51–59, 62, 64, 66, 67, 69–72, 75–79, 86–92, 96–99, 101, 103–105, 107–110, 120, 122–129, 131, 135 and 144–147 were found to have significant activity.

Aphid Tests

Broad bean plants in the 6 to 8 leaf stage were removed from pots and their roots were washed free of soil. Each was placed in a flask containing 100 ml of a water solution of the test compound. The plant stems were wrapped with non-absorbent cotton fitted snugly into the neck of the flask to prevent possible fumigant action by the test compound. The flask was positioned under a wooden stage with the stem of the plant extending up through a slot in the stage. A 6"×6" square of paper was placed flat on the stage around the stem of the plant. A plastic ring 5 inches in diameter and 2 inches high, coated on the inside with petroleum jelly, was placed around the plant to prevent the aphids from escaping. 50 to 100 aphids were placed within each ring. Then the plant was held for 48 hours at 85° F., and 50% relative humidity when mortality in the mites was determined visually. A series of different dosages of the test compound in the water were used, and the $LC_{50}$ dosage (the dosage in parts per million by weight of the test chemical in the water required to effect fifty percent kill of the aphids) was determined.

Compounds Nos. 1, 3, 17, 18, 21, 39, 44, 48, 52, 55, 56, 59, 66, 69, 71, 72, 75–79, 86–92, 97, 98, 101, 105, 107, 110, 114, 116, 122–129, 131, 133–135, 144 and 147 were found to have significant activity.

I claim:
1. A compound of the formula:

$$\begin{array}{c} X \quad R^2 \\ \| \quad | \\ R-P-N-SO_2-R^3 \\ | \\ S-R^1 \end{array}$$

wherein X is oxygen or sulfur;
R is alkyl or alkenyl of up to twenty carbon atoms, phenyl or phenalkyl of up to ten carbon atoms;
$R^1$ is alkyl, or alkenyl of up to six carbon atoms, or phenalkyl of up to ten carbon atoms;
$R^2$ is alkyl, alkenyl, alkynyl, haloalkyl or alkylthioalkyl of up to ten carbon atoms; napthyl, pyridyl, or thienyl; phenyl, or phenalkyl or phenalkenyl of up to ten carbon atoms, which may be substituted on the ring by from one to three substituents selected from halogen, methyl, methoxy, nitro, amino, mono- and dialkylamino, and mono- and dialkylaminocarbonyl wherein each alkyl moiety contains from one to four carbon atoms;
$R^3$ is
(a) one of the moieties represented by $R^2$ or is (b) a moiety $-N\begin{matrix} R^4 \\ \diagdown \\ R^5 \end{matrix}$ wherein $R^4$ is alkyl of one to four carbon atoms, phenyl, or phenalkyl of up to ten carbon atoms, $R^5$ is hydrogen or one of the moieties represented by $R^4$, or $R^4$ and $R^5$ together with the interjacent nitrogen atom represent 1-piperidino, 2-(ethoxycarbonyl)-1-piperidino, or 4-morpholino.

2. A method for controlling insects and/or acarids at a locus that comprises subjecting them to an effective dosage of a compound of claim 1.

3. A composition adapted to the control of insects and acarid that comprises an effective amount of a compound of claim 1 together with a carrier and a surface-active agent.

* * * * *